United States Patent

(12) United States Patent
Koyakumaru et al.

(10) Patent No.: US 7,358,400 B2
(45) Date of Patent: Apr. 15, 2008

(54) PROCESS FOR PRODUCING CYCLOPROPANE MONOACETAL DERIVATIVE AND INTERMEDIATE THEREFOR

(75) Inventors: Kenichi Koyakumaru, Bizen (JP); Shingo Ueyama, Kurashiki (JP); Katsuji Ujita, Kitakanbara-gun (JP); Tatsuhiko Hayashibara, Kurashiki (JP); Naoshi Nakagawa, Tokyo (JP); Toshifumi Akiba, Tokyo (JP); Tatsuru Saito, Tokyo (JP)

(73) Assignees: Kuraray Co., Ltd., Kurashiki-shi (JP); Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/593,129

(22) PCT Filed: Mar. 25, 2005

(86) PCT No.: PCT/JP2005/006407

§ 371 (c)(1),
(2), (4) Date: Sep. 18, 2006

(87) PCT Pub. No.: WO2005/095318

PCT Pub. Date: Nov. 13, 2005

(65) Prior Publication Data
US 2007/0191643 A1 Aug. 16, 2007

(30) Foreign Application Priority Data
Mar. 31, 2004 (JP) ............................. 2004-104862

(51) Int. Cl.
C07C 45/61 (2006.01)
C07C 49/04 (2006.01)

(52) U.S. Cl. ........................................ 568/348; 568/418
(58) Field of Classification Search .................... None
See application file for complete search history.

(56) References Cited

U.S. PATENT DOCUMENTS

2004/0019223 A1   1/2004  Nakayama et al.

FOREIGN PATENT DOCUMENTS

| JP | 08-133997 A | 5/1996 |
| JP | 2002-105029 A | 4/2002 |
| JP | 2002-322114 A | 11/2002 |
| WO | WO 02/14278 A1 | 2/2002 |

*Primary Examiner*—Sikarl A. Witherspoon
(74) *Attorney, Agent, or Firm*—Leydig, Voit & Mayer, Ltd.

(57) ABSTRACT

A method of industrially advantageously producing a cyclopropane monoacetal derivative represented by the formula (III) conveniently and also in a fewer steps by reacting a halogenated unsaturated carbonyl compound represented by the formula (II) with an alcoholate.

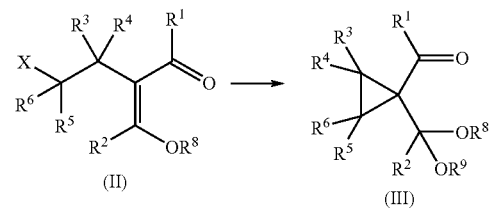

wherein each symbol is as defined in the specification.

6 Claims, No Drawings

PROCESS FOR PRODUCING CYCLOPROPANE MONOACETAL DERIVATIVE AND INTERMEDIATE THEREFOR

TECHNICAL FIELD

The present invention relates to novel production methods of cyclopropane monoacetal derivatives usable as raw material for antibacterial agents, and intermediate compounds therefor.

BACKGROUND ART

Cyclopropane monoacetal derivatives represented by the below-mentioned formula (III) (hereinafter sometimes to be abbreviated as cyclopropane monoacetal derivative (III)), for example, 1-(dialkoxymethyl)cyclopropanecarbaldehyde represented by the formula (IV) as a known compound

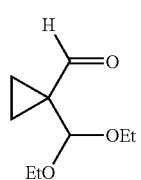

are useful as raw material for antibacterial agents. A compound represented by the formula (IV) is synthesized, for example, by monoacetalization of a dicarbonyl compound corresponding to said compound in the presence of an acid catalyst and using an ortho ester, and led, via several steps, to amino-substituted azaspiroalkane which is an intermediate for synthetic antibacterial agents (see WO02/14278). However, this method is associated with problems of inability to avoid contamination with a remaining dicarbonyl compound, which is a starting material, a diacetal compound produced by an over reaction, and the like.

DISCLOSURE OF THE INVENTION

An object of the present invention is to provide a method of industrially advantageously producing a cyclopropane monoacetal derivative, particularly 1-(dialkoxymethyl)cyclopropanecarbaldehyde, conveniently and also in a fewer steps.

The present inventors have conducted intensive studies in an attempt to achieve the above-mentioned object and found a completely new method of producing cyclopropane monoacetal derivative (III) from a novel halogenated unsaturated carbonyl compound represented by the below-mentioned formula (II) (hereinafter sometimes to be abbreviated as halogenated unsaturated carbonyl compound (II)). By this production method, cyclopropane monoacetal derivative (III) can be industrially advantageously obtained conveniently and also in a fewer steps. Moreover, they have also found that halogenated unsaturated carbonyl compound (II) can be obtained by reacting alkoxy-cyclic ether represented by the below-mentioned formula (I) (hereinafter sometimes to be abbreviated as alkoxy-cyclic ether (I)) with a halogenating agent. They have found that, while sulfite diester or sulfate diester is formed as by-product when thionyl halide or sulfuryl halide is used as a halogenating agent in the reaction of alkoxy-cyclic ether (I) with a halogenating agent, the by-product can be easily removed by treating the reaction mixture with an aqueous alkali solution after completion of the reaction, which resulted in the completion of the present invention. Accordingly, the present invention provides the following.

[1] A method of producing a cyclopropane monoacetal derivative represented by the formula (III)

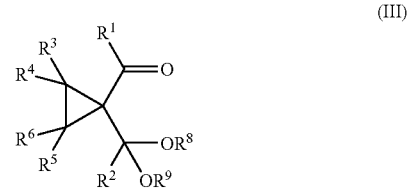

wherein $R^1$, $R^2$, $R^3$, $R^4$, $R^5$ and $R^6$ each independently represents a hydrogen atom, a saturated hydrocarbon group optionally having substituent(s), an aryl group optionally having substituent(s), an alkenyl group or an aralkyl group, $R^8$ represents a saturated hydrocarbon group optionally having substituent(s), an aryl group optionally having substituent(s) or an aralkyl group, and $R^9$ represents a saturated hydrocarbon group optionally having substituent(s), an aryl group optionally having substituent(s) or an aralkyl group, which comprises reacting a halogenated unsaturated carbonyl compound represented by the formula (II)

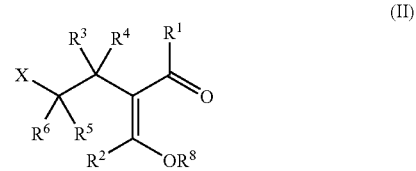

wherein $R^1$, $R^2$, $R^3$, $R^4$, $R^5$, $R^6$ and $R^8$ represent as defined above, and X represents a halogen atom, with an alcoholate.

[2] The method of the above-mentioned [1], wherein the halogenated unsaturated carbonyl compound (II) is obtained by reacting an alkoxy-cyclic ether represented by the formula (I)

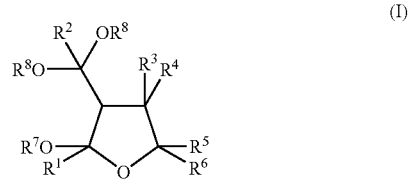

wherein $R^1$, $R^2$, $R^3$, $R^4$, $R^5$, $R^6$ and $R^8$ represent as defined above, and $R^7$ represents a saturated hydrocarbon group optionally having substituent(s), an aryl group optionally having substituent(s) or an aralkyl group, with a halogenating agent.

[3] The method of the above-mentioned [2], wherein the halogenating agent is thionyl halide or sulfuryl halide.

[4] The method of the above-mentioned [2], wherein the halogenating agent is acyl halide.

[5] The method of the above-mentioned [2], wherein the halogenating agent is halogenated carbonate.

[6] A halogenated unsaturated carbonyl compound (II).

According to the present invention, a cyclopropane monoacetal derivative, particularly 1-(dialkoxymethyl)cyclopropanecarbaldehyde, can be industrially advantageously produced conveniently and also in a fewer steps.

BEST MODE FOR EMBODYING THE INVENTION

The saturated hydrocarbon group represented by $R^1$, $R^2$, $R^3$, $R^4$, $R^5$, $R^6$, $R^7$, $R^8$ or $R^9$ is linear, branched or cyclic, and the carbon number thereof is preferably 1 to 12, more preferably 1 to 6, and, for example, an alkyl group such as methyl group, ethyl group, propyl group, isopropyl group, butyl group, isobutyl group, tert-butyl group, hexyl group, octyl group, dodecyl group and the like; a cycloalkyl group such as cyclopentyl group, cyclohexyl group and the like; and the like can be mentioned. These saturated hydrocarbon groups may have substituent(s), and as such substituent, for example, an aryl group having 6 to 10 carbon atoms such as phenyl group optionally substituted by substituent(s) selected from an alkyl group having 1 to 6 carbon atoms such as methyl group and the like, an alkoxyl group having 1 to 6 carbon atoms such as methoxy group and a halogen atom such as chlorine atom and the like; an alkoxyl group having 1 to 6 carbon atoms such as methoxy group, ethoxy group, propoxy group, butoxy group and the like; and the like can be mentioned.

The aryl group represented by $R^1$, $R^2$, $R^3$, $R^4$, $R^5$, $R^6$, $R^7$, $R^8$ or $R^9$ preferably has 6 to 14, more preferably 6 to 10, carbon atoms and, for example, phenyl group, naphthyl group, anthracenyl group and the like can be mentioned. These aryl groups may have substituent(s) and as such substituent, for example, a linear, branched or cyclic saturated hydrocarbon group having 1 to 12 carbon atoms, such as methyl group, ethyl group, propyl group, isopropyl group, butyl group, isobutyl group, tert-butyl group, hexyl group, octyl group, dodecyl group, cyclopentyl group, cyclohexyl group and the like; an aryl group having 6 to 14 carbon atoms and optionally having substituent(s) (e.g., an alkyl group having 1 to 3 carbon atoms, an alkoxyl group having 1 to 3 carbon atoms, a halogen atom, nitro group and the like), such as phenyl group, tolyl group, methoxyphenyl group, chlorophenyl group, bromophenyl group, nitrophenyl group, naphthyl group, anthracenyl group and the like; and the like can be mentioned.

The alkenyl group represented by $R^1$, $R^2$, $R^3$, $R^4$, $R^5$ or $R^6$ is linear or branched and preferably has 2 to 12, more preferably 2 to 6, carbon atoms. For example, allyl group and the like can be mentioned.

The aralkyl group represented by $R^1$, $R^2$, $R^3$, $R^4$, $R^5$, $R^6$, $R^7$, $R^8$ or $R^9$ preferably has 7 to 18, more preferably 7 to 12, carbon atoms. For example, benzyl group and the like can be mentioned.

The halogen atom represented by X is chlorine atom, fluorine atom, bromine atom or iodine atom, with particular preference given to chlorine atom, bromine atom and iodine atom.

The present invention is described in detail in the following.

The step to obtain halogenated unsaturated carbonyl compound (II) (Step 1) by reacting alkoxy-cyclic ether (I) with a halogenating agent is first explained.

The alkoxy-cyclic ether (I) to be used in the present invention can be produced according to a known method and, for example, alkoxy-cyclic ether wherein $R^1$ and $R^2$ are hydrogen atoms can be easily obtained by reacting the corresponding 2,3-dihydrofuran with orthoformate in the presence of a Lewis acid according to the method described in JP-A-8-133997.

As the halogenating agent to be used in Step 1, for example, thionyl halides such as thionyl chloride, thionyl bromide and the like; sulfuryl halides such as sulfuryl chloride, sulfuryl bromide and the like; acyl halides such as acetyl chloride, propionyl chloride, butyryl chloride, benzoyl chloride and the like; halogenated carbonates such as methyl chlorocarbonate, ethyl chlorocarbonate, propyl chlorocarbonate, isopropyl chlorocarbonate, butyl chlorocarbonate, isobutyl chlorocarbonate and the like; and the like can be mentioned.

When the halogenating agent to be used in Step 1 is thionyl halide or sulfuryl halide, its amount to be used is preferably within the range of 0.4 to 1.5 mol, more preferably within the range of 0.5 to 1.1 mol, per 1 mol of the alkoxy-cyclic ether (I). The time for addition of thionyl halide or sulfuryl halide is generally 0.5 to 48 hr and, from the aspect of production efficiency, preferably 1 to 20 hr. When thionyl halide or sulfuryl halide is used, Step 1 can be performed at a temperature within the range of −20° C. to 150° C. However, it is preferably performed particularly within the temperature range of 70° C. to 150° C. from the aspect of yield and reaction time. While the reaction time may vary depending on the reaction temperature, it is generally within the range of 1 to 24 hr after completion of the addition.

When the halogenating agent to be used in Step 1 is acyl halide or halogenated carbonate, its amount to be used is preferably within the range of 0.8 to 5 mol, more preferably within the range of 1 to 3 mol, per 1 mol of the alkoxy-cyclic ether (I). The time for addition of acyl halide or halogenated carbonate is generally 0.5 to 24 hr and, from the aspect of production efficiency, preferably 1 to 10 hr. When the halogenating agent to be used is acyl halide or halogenated carbonate, the temperature in Step 1 is preferably 0° C. to 150° C., more preferably 40° C. to 120° C. While the reaction time may vary depending on the reaction temperature, it is generally within the range of 1 to 24 hr after completion of the addition.

Step 1 is preferably performed in the presence of a solvent. Usable solvents are not particularly limited as long as they do not adversely affect the reaction and, for example, aromatic hydrocarbons such as benzene, toluene, xylene, chlorobenzene and the like; aliphatic hydrocarbons such as pentane, hexane, cyclohexane, octane and the like; halogenated hydrocarbons such as dichloromethane, chloroform, dichloroethane and the like; esters such as methyl acetate, ethyl acetate, n-propyl acetate, n-butyl acetate and the like; and the like can be mentioned. While the amount of the solvent to be used is not particularly limited, it is preferably within the range of 0.5- to 50-fold mass, more preferably 1- to 10-fold mass, based on the alkoxy-cyclic ether (I).

Step 1 can be performed by mixing alkoxy-cyclic ether (I) with a halogenating agent in a solvent. A catalyst may be further added depending on the kind of the halogenating agent to be used. As the catalyst usable here, organic bases such as pyridine and the like and alcohols such as ethanol and the like can be mentioned. When the catalyst is added, its amount is preferably within the range of 0.1 to 20 mol %, more preferably within the range of 1 to 5 mol %, based on the alkoxy-cyclic ether (I).

After completion of Step 1, the reaction solution contains halogenated unsaturated carbonyl compound (II) and, when thionyl halide or sulfuryl halide is used as a halogenating agent, the reaction solution contains by-products such as sulfite diester, sulfate diester and the like. The solution may be directly used for the next step (Step 2) mentioned below. Where necessary, after completion of Step 1, halogenated unsaturated carbonyl compound (II) can be isolated and purified by an ordinary purification operation such as distillation, column chromatography and the like. For example, after completion of Step 1, halogenated unsaturated carbonyl compound (II) can be isolated by adding the obtained reaction solution to an aqueous alkali solution (e.g., aqueous sodium hydrogen carbonate solution), stirring the mixture at preferably below 30° C., allowing separating, concentrating the obtained organic layer (e.g., toluene layer), and distilling the concentrate under reduced pressure.

Now, a step to obtain cyclopropane monoacetal derivative (III) (Step 2) by reacting halogenated unsaturated carbonyl compound (II) with alcoholate is explained.

The alcoholate to be used in Step 2 can be obtained by adding an alkali metal or alkaline earth metal such as lithium, sodium, potassium, calcium, magnesium or the like, or a base to alcohol: $R^9$—OH wherein $R^9$ represents as defined above. As such base, for example, alkali metal hydrides such as lithium hydride, sodium hydride, potassium hydride and the like; alkali metal hydroxides such as lithium hydroxide, sodium hydroxide, potassium hydroxide and the like; alkaline earth metal hydrides such as calcium hydride and the like; alkaline earth metal hydroxides such as calcium hydroxide, magnesium hydroxide and the like; organic bases such as pyridine, 1,8-diazabicyclo[5.4.0]-7-undecene, tertiary amines having a saturated hydrocarbon group having 1 to 8 carbon atoms such as trimethylamine, triethylamine, tripropylamine, trin-butylamine, trin-pentylamine, trin-hexylamine, trin-octylamine and the like; and the like can be used. The alcoholate may be prepared in the reaction system, or a separately prepared alcoholate may be used. The amount of the alcoholate to be used is preferably within the range of 0.5 to 2 mol, more preferably within the range of 0.8 to 1.1 mol, per 1 mol of the halogenated unsaturated carbonyl compound (II).

When the alcoholate is prepared independently, the amount of the alkali metal, alkaline earth metal or base is preferably within the range of 0.5 to 2 mol, more preferably within the range of 0.8 to 1.1 mol, per 1 mol of the halogenated unsaturated carbonyl compound (II) to be used in Step 2. The amount of the alcohol is preferably within the range of 0.5 to 50 mol, more preferably within the range of 1 to 20 mol, per 1 mol of the halogenated unsaturated carbonyl compound (II) to be used in Step 2.

The alcoholate to be used in Step 2 is industrially produced and is commercially available. Such product can also be used. The form thereof may be a solid such as powder, pellet and the like, or a solution dissolved in a corresponding alcohol. The amount of the alcohol necessary for dissolution is preferably within the range of 0.5 mol to 50 mol, more preferably within the range of 1 mol to 20 mol, per 1 mol of the halogenated unsaturated carbonyl compound (II). While the concentration of the alcoholate varies depending on the solubility in the alcohol to be used, it is preferably 1 to 50 mass %, more preferably 5 to 30 mass %. When the alcoholate is a solid, the corresponding alcohol can be present in the reaction system as necessary.

Step 2 is preferably performed in the presence of a solvent. Usable solvents are not particularly limited as long as they do not adversely affect the reaction and, for example, aromatic hydrocarbons such as benzene, toluene, xylene, chlorobenzene and the like; aliphatic hydrocarbons such as pentane, hexane, cyclohexane, octane and the like; halogenated hydrocarbons such as dichloromethane, chloroform, dichloroethane and the like; esters such as methyl acetate, ethyl acetate, n-propyl acetate, n-butyl acetate and the like; and the like can be mentioned. While the amount of the solvent to be used is not particularly limited, it is preferably within the range of 0.5- to 50-fold mass, more preferably 1- to 10-fold mass, based on the halogenated unsaturated carbonyl compound (II).

The temperature in Step 2 is preferably within the range of −78° C. to 50° C., more preferably −40° C. to 30° C. While the reaction time may vary depending on the reaction temperature, it is generally within the range of 1 to 48 hr.

Step 2 can be performed by mixing halogenated unsaturated carbonyl compound (II) with an alcoholate in a solvent. Depending on the stability of the produced cyclopropane monoacetal derivative (III) to the alcoholate, the alcoholate can be added to a mixed solution of halogenated unsaturated carbonyl compound (II), which is a starting material, and the solvent.

When the halogenating agent to be used in Step 1 is thionyl halide or sulfuryl halide, the reaction solution obtained after completion of Step 1 contains, besides halogenated unsaturated carbonyl compound (II), sulfite diester or sulfate diester, which is a by-product. When this reaction solution is directly used in Step 2 without purification, these by-products (sulfite diester and sulfate diester) can be removed by adding an aqueous alkali solution to the obtained reaction solution after completion of Step 2, and heating the mixture to 30° C. to 150° C. for decomposition. The aqueous alkali solution to be used is preferably an aqueous solution of an alkali metal salt such as lithium hydroxide, sodium hydroxide, potassium hydroxide, lithium carbonate, sodium carbonate, potassium carbonate and the like. The amount of the aqueous alkali solution to be used is preferably within the range of 1- to 20-fold mol of sulfite diester or sulfate diester, based on the alkali metal salt contained therein. The concentration of the aqueous alkali solution is preferably within the range of 1 to 50 mass %, more preferably within the range of 5 to 20 mass %. The decomposition temperature is more preferably within the range of 40° C. to 80° C. While the decomposition time is not particularly limited as long as the temperature is as mentioned above, it is preferably 5 min to 24 hr, particularly preferably within the range of 1 to 10 hr, from the aspect of production efficiency.

The reaction solution thus obtained can be subjected to general work-up in the organic synthesis chemistry such as neutralization, extraction and the like, and purified by distillation and the like to isolate cyclopropane monoacetal derivative (III). The obtained cyclopropane monoacetal derivative (III) can be led to amino-substituted azaspiroalkane, which is an intermediate for synthetic antibacterial agents, by a known method, such as the method described in WO02/14278 or a method analogous thereto.

EXAMPLES

The present invention is explained in detail in the following by referring to Reference Example and Examples, which are not to be construed as limitative.

Reference Example 1

Production of 3-(diethoxymethyl)-2-ethoxytetrahydrofuran

Triethyl orthoformate (1465 g, 9.89 mol) was added to a 3 L three-necked flask equipped with a thermometer and a stirrer, and cooled to 10° C. to 12° C. Iron chloride (1.172 g, 0.00723 mol) was added as a catalyst and the mixture was stirred at the same temperature for 30 min. Then, 2,3-dihydrofuran (630 g, 8.99 mol) was added dropwise to the mixture over 5.5 hr while maintaining the inner temperature at 10° C. to 15° C., and the mixture was stirred at the same temperature for 1 hr. The reaction solution was analyzed by gas chromatography. As a result, 3-(diethoxymethyl)-2-ethoxytetrahydrofuran (1837 g, 8.42 mol) was produced. The yield based on 2,3-dihydrofuran was 93.7%. The reaction solution was transferred to a flask equipped with a distillation column (inner diameter 2.5 cm, height 30 cm) packed with ceramic Raschig ring, and distilled under reduced pressure to give 3-(diethoxymethyl)-2-ethoxytetrahydrofuran (1348.7 g, purity 99.7%) as a distilled fraction (a top temperature of 93° C. to 94° C. at a reduced pressure level of 0.67 kPa (5 mmHg)).

Example 1

Production of 4-chloro-2-ethoxymethylidenebutanal

Toluene (466 g) and 3-(diethoxymethyl)-2-ethoxytetrahydrofuran (200.0 g, 0.916 mol) obtained by the method of Reference Example 1 were added to a 2 L three-necked flask equipped with a thermometer and a stirrer, and the mixture was heated to 90° C. to 95° C. under a nitrogen atmosphere. Thionyl chloride (114.5 g, 0.962 mol) was added dropwise to the mixture over 4 hr. After completion of the dropwise addition, the mixture was stirred for 1 hr. The obtained reaction solution was added to a 12 mass % aqueous sodium hydrogen carbonate solution (370.6 g) while maintaining the liquid temperature below 30° C., and the mixture was stirred for 30 min and partitioned. The aqueous layer was extracted with toluene (285 g), the extract was combined with the organic layer obtained earlier to give a toluene solution (898 g). The toluene solution was analyzed by gas chromatography. As a result, 4-chloro-2-ethoxymethylidenebutanal (126.6 g) was produced. The yield based on 3-(diethoxymethyl)-2-ethoxytetrahydrofuran was 85.2%. The toluene solution was concentrated and the concentrate was distilled under reduced pressure to give crude 4-chloro-2-ethoxymethylidenebutanal (54.9 g, purity 95.1%) having the following property.

$^1$H-NMR (CDCl$_3$, ppm, TMS) δ: 1.40 (t, 3H, J=7 Hz), 2.65-2.80 (m, 2H), 3.50-3.65 (m, 2H), 4.20 (q, 2H, J=7 Hz), 7.10 (s, 1H), 9.20 (s, 1H).

Example 2

Production of 1-(diethoxymethyl)cyclopropanecarbaldehyde

Toluene (100 g) and crude 4-chloro-2-ethoxymethylidenebutanal (50.01 g, pure content 47.5 g, 0.292 mol) obtained in Example 1 were added to a 300 ml three-necked flask equipped with a thermometer and a stirrer, and the mixture was cooled to 10° C. An ethanol solution of sodium ethoxide (101.5 g, 20 mass %, 0.298 mol) was added dropwise while maintaining the inner temperature at 10° C. to 15° C. The obtained reaction solution was added dropwise to degassed water (99.9 g) while maintaining at 10° C. to 15° C., and the mixture was adjusted to pH=9-10 with a 0.5 N aqueous hydrochloric acid solution and a 0.05 N aqueous sodium hydroxide solution. The organic layer was partitioned. The aqueous layer was extracted with toluene (80 g), and the extract and the organic layer obtained earlier were combined and concentrated under reduced pressure below 70° C. to give crude 1-(diethoxymethyl)cyclopropanecarbaldehyde (53.0 g, pure content 47.3 g, 0.275 mol, yield 92.3%).

Of the obtained crude 1-(diethoxymethyl)cyclopropanecarbaldehyde, 50 g was charged together with trin-octylamine (1.20 g) in a flask equipped with a 20 cm vigreux column, and distilled under reduced pressure to give 37.3 g of 1-(diethoxymethyl)cyclopropanecarbaldehyde (purity 99.1%) as a distilled fraction (a top temperature of 73° C. to 74° C. at a reduced pressure level of 1.2 kPa (9 mmHg)).

Example 3

Production of 4-chloro-2-ethoxymethylidenebutanal

Toluene (583 g) and 3-(diethoxymethyl)-2-ethoxytetrahydrofuran (250.8 g, 1.15 mol) obtained by the method of Reference Example 1 were added to a 2 L three-necked flask equipped with a thermometer and a stirrer, and the mixture was heated under reflux in a nitrogen atmosphere (liquid temperature 117° C.). Thionyl chloride (143.1 g, 1.20 mol) was added dropwise to the mixture over 4 hr. After completion of the dropwise addition, the mixture was stirred for 1 hr, cooled, and the reaction solution was analyzed by gas chromatography. As a result, 4-chloro-2-ethoxymethylidenebutanal (161.1 g, 0.991 mol, yield 86.2%) was produced.

Example 4

Production of 4-chloro-2-ethoxymethylidenebutanal

Toluene (116.6 g) and 3-(diethoxymethyl)-2-ethoxytetrahydrofuran (50.16 g, 0.229 mol) obtained by the method of Reference Example 1 were added to a 300 ml three-necked flask equipped with a thermometer and a stirrer, and the mixture was heated to 85° C. to 90° C. under a nitrogen atmosphere. Thionyl chloride (13.64 g, 0.115 mol) was added dropwise to the mixture over 4 hr to allow reaction, and thionyl chloride (2.73 g) was further added. The mixture was stirred at the same temperature for 1 hr and cooled to give a reaction solution containing 4-chloro-2-ethoxymethylidenebutanal (151.7 g, pure content 32.5 g, yield 87.3%).

Example 5

Production of 4-chloro-2-ethoxymethylidenebutanal

Toluene (468 g) and 3-(diethoxymethyl)-2-ethoxytetrahydrofuran (200.5 g, 0.916 mol) obtained in Reference Example 1 were added to a 1 L three-necked flask equipped with a thermometer and a stirrer, and the mixture was heated to 85° C. to 90° C. under a nitrogen atmosphere. Thionyl chloride (109.0 g, 0.916 mol) was added dropwise to the mixture over 4 hr. After the dropwise addition, the mixture was stirred at the same temperature for 1 hr and cooled. The reaction solution was adjusted to pH 8-9 with water (275 g) containing sodium carbonate (10.6 g) while maintaining below 30° C. The organic layer was partitioned and concentrated below 70° C. under reduced pressure to give crude 4-chloro-2-ethoxymethylidenebutanal (189.13 g, pure content 116.0 g, 0.713 mol, yield 78%). The diethyl sulfite content in the obtained crude 4-chloro-2-ethoxymethylidenebutanal was 16.11 g (0.117 mol).

Example 6

Production of 4-chloro-2-ethoxymethylidenebutanal with Acetyl Chloride 3-(Diethoxymethyl)-2-ethoxytetrahydrofuran (20.01 g, 91.7 mmol) obtained by the method of Reference Example 1, toluene (46.02 g) and ethanol (126.2 mg, 2.74 mmol) were added to a 100 ml three-necked flask equipped with a thermometer, a stirrer and a dimroth condenser, and the mixture was heated to 90° C. under a nitrogen atmosphere. Acetyl chloride (15.11 g, 192.5 mmol) was added dropwise to the mixture over 1 hr. After completion of the dropwise addition, the mixture was reacted at 80° C. for 6 hr and analyzed by gas chromatography. As a result, 4-chloro-2-ethoxymethylidenebutanal (13.8 g, 84.9 mmol, yield 92.6%) was produced.

Example 7

Production of 4-chloro-2-ethoxymethylidenebutanal with Acetyl Chloride

The operation was conducted in the same manner as in Example 6 except that the acetyl chloride was added over 4 hr. As a result, the yield of 4-chloro-2-ethoxymethylidenebutanal was 89.7%.

Example 8

Production of 4-chloro-2-ethoxymethylidenebutanal with Ethyl Chlorocarbonate 3-(Diethoxymethyl)-2-ethoxytetrahydrofuran (20.03 g, 91.8 mmol) obtained by the method of Reference Example 1, toluene (46.0 g) and pyridine (0.22 g, 2.8 mmol) were added to a 100 ml three-necked flask equipped with a thermometer, a stirrer and a dimroth condenser, and the mixture was heated to 100° C. to 106° C. under a nitrogen atmosphere. Ethyl chlorocarbonate (19.92 g, 183.5 mmol, 2-fold mol relative to 3-(diethoxymethyl)-2-ethoxytetrahydrofuran) was added dropwise to the mixture over 1 hr. After completion of the dropwise addition, the mixture was reacted at the same temperature for 6 hr, and the reaction solution was analyzed by gas chromatography. As a result, the conversion ratio of 3-(diethoxymethyl)-2-ethoxytetrahydrofuran was 100%, and 4-chloro-2-ethoxymethylidenebutanal (14.3 g, 87.9 mmol, yield 95.8%) was produced.

Example 9

Production of 4-chloro-2-ethoxymethylidenebutanal with Ethyl Chlorocarbonate

The operation was conducted in the same manner as in Example 8 except that the amount of ethyl chlorocarbonate was 1.3-fold mol relative to the starting material. As a result, the conversion ratio of 3-(diethoxymethyl)-2-ethoxytetrahydrofuran was 97.1%, and 4-chloro-2-ethoxymethylidenebutanal was obtained in a yield of 90.5%.

Example 10

Production of 1-(diethoxymethyl)cyclopropanecarbaldehyde

Crude 4-chloro-2-ethoxymethylidenebutanal (189.13 g, pure content 116.0 g, 0.713 mol) obtained in Example 5 and toluene (232 g) were added to a 2 L four-necked flask equipped with a thermometer and a stirrer, and the mixture was cooled to 10° C. to 15° C. with stirring. An ethanol solution of sodium ethoxide (311.6 g, 14.6 mass %, 0.669 mol) was added dropwise to the mixture while maintaining the inner temperature at 10° C. to 15° C. After completion of the dropwise addition, the reaction solution was added dropwise to water (232 g) while maintaining at 10° C. to 15° C. to allow partitioning to give a solution containing 1-(diethoxymethyl)cyclopropanecarbaldehyde (567.3 g, pure content 105.9 g, 0.614 mol, yield 86.3%). Of the solution, 425.6 g (pure content 79.4 g, 0.461 mol; diethyl sulfite content 12.09 g, 87.5 mmol) was stirred together with sodium hydroxide (28.4 g, 0.71 mol) and water (261 g) at 70° C. for 4 hr to decompose diethyl sulfite, and the mixture was partitioned. The aqueous layer after partitioning was extracted with toluene (79.4 g), and the extract was combined with the organic layer obtained earlier. The combined organic layer was washed with water (87 g), and concentrated below 70° C. under reduced pressure. As a result, 105.63 g of crude 1-(diethoxymethyl)cyclopropanecarbaldehyde (content 76.0 g, 0.441 mol) was obtained. The yield based on 4-chloro-2-ethoxymethylidenebutanal was 82.4%.

Example 11

Production of 1-(diethoxymethyl)cyclopropanecarbaldehyde

Under a nitrogen atmosphere, toluene (10.0 g), ethanol (4.16 g, 90.3 mmol) and 4-chloro-2-ethoxymethylidenebutanal (5.00 g, pure content 4.80 g, 29.6 mmol) obtained in Example 1 were added to a 50 ml three-necked flask equipped with a thermometer and a stirrer, and the mixture was cooled to −30° C. to −25° C. An ethanol solution of sodium hydroxide (11.0 g, 11.0 mass %, 30.2 mmol) was added dropwise to the mixture over 1 hr while maintaining at −30° C. to −25° C. After completion of the dropwise addition, the mixture was stirred at the same temperature for 1 hr, and the reaction solution was analyzed by gas chromatography. As a result, 1-(diethoxymethyl)cyclopropanecarbaldehyde (4.25 g, 24.7 mmol, yield 83.4%) was produced.

Example 12

Production of 1-(diethoxymethyl)cyclopropanecarbaldehyde

Under a nitrogen atmosphere, toluene (10.0 g), ethanol (4.16 g, 90.3 mmol) and 4-chloro-2-ethoxymethylidenebutanal (5.00 g, pure content 4.80 g, 29.6 mmol) obtained in Example 1 were added to a 50 ml three-necked flask equipped with a thermometer and a stirrer, and the mixture was heated to 40° C. to 45° C. An ethanol solution of sodium hydroxide (11.0 g, 11.0 mass %, 30.2 mmol) was added dropwise to the mixture over 1 hr while maintaining at 40° C. to 45° C. After completion of the dropwise addition, the mixture was stirred at the same temperature for 1 hr, and the reaction solution was analyzed by gas chromatography. As a result, 1-(diethoxymethyl)cyclopropanecarbaldehyde (4.70 g, 27.3 mmol, yield 92.2%) was produced.

INDUSTRIAL APPLICABILITY

The cyclopropane monoacetal derivative that can be produced by the method of the present invention is useful as a raw material for amino-substituted azaspiroalkane to be a raw material for synthetic antibacterial agents.

This application is based on a patent application No. 2004-104862 filed in Japan, the contents of which are incorporated in full herein by this reference.

The invention claimed is:

1. A method of producing a cyclopropane monoacetal derivative represented by the formula (III)

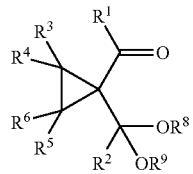

(III)

wherein $R^1$, $R^2$, $R^3$, $R^4$, $R^5$ and $R^6$ each independently represents a hydrogen atom, a saturated hydrocarbon group optionally having substituent(s), an aryl group optionally having substituent(s), an alkenyl group or an aralkyl group, $R^8$ represents a saturated hydrocarbon group optionally having substituent(s), an aryl group optionally having substituent(s) or an aralkyl group, and $R^9$ represents a saturated hydrocarbon group optionally having substituent(s), an aryl group optionally having substituent(s) or an aralkyl group, which comprises reacting a halogenated unsaturated carbonyl compound represented by the formula (II)

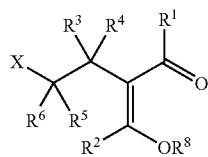

(II)

wherein $R^1$, $R^2$, $R^3$, $R^4$, $R^5$, $R^6$ and $R^8$ represent as defined above, and X represents a halogen atom, with an alcoholate.

2. The method of claim 1, wherein the halogenated unsaturated carbonyl compound represented by the formula (II)

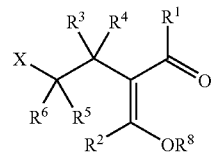

(II)

wherein $R^1$, $R^2$, $R^3$, $R^4$, $R^5$ and $R^6$ each independently represents a hydrogen atom, a saturated hydrocarbon group optionally having substituent(s), an aryl group optionally having substituent(s), an alkenyl group or an aralkyl group, $R^8$ represents a saturated hydrocarbon group optionally having substituent(s), an aryl group optionally having substituent(s) or an aralkyl group, and X represents a halogen atom, is obtained by reacting an alkoxy-cyclic ether represented by the formula (I)

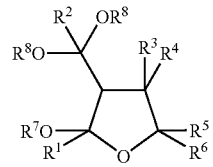

(I)

wherein $R^1$, $R^2$, $R^3$, $R^4$, $R^5$, $R^6$ and $R^8$ represent as defined above, and $R^7$ represents a saturated hydrocarbon group optionally having substituent(s), an aryl group optionally having substituent(s) or an aralkyl group, with a halogenating agent.

3. The method of claim 2, wherein the halogenating agent is thionyl halide or sulfuryl halide.

4. The method of claim 2, wherein the halogenating agent is acyl halide.

5. The method of claim 2, wherein the halogenating agent is halogenated carbonate.

6. A halogenated unsaturated carbonyl compound represented by the formula (II):

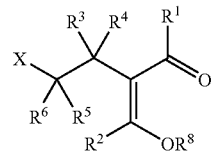

(II)

wherein $R^1$, $R^2$, $R^3$, $R^4$, $R^5$ and $R^6$ each independently represents a hydrogen atom, a saturated hydrocarbon group optionally having substituent(s), an aryl group optionally having substituent(s), an alkenyl group or an aralkyl group, $R^8$ represents a saturated hydrocarbon group optionally having substituent(s), an aryl group optionally having substituent(s) or an aralkyl group, and X represents a halogen atom.

* * * * *

UNITED STATES PATENT AND TRADEMARK OFFICE
CERTIFICATE OF CORRECTION

PATENT NO. : 7,358,400 B2
APPLICATION NO. : 10/593129
DATED : April 15, 2008
INVENTOR(S) : Koyakumaru et al.

Page 1 of 1

It is certified that error appears in the above-identified patent and that said Letters Patent is hereby corrected as shown below:

On the Title Page

Item (87) PCT Pub. Date: Nov. 13, 2005 should read:

Item (87) PCT Pub. Date: Oct. 13, 2005

Signed and Sealed this

Eleventh Day of November, 2008

JON W. DUDAS
*Director of the United States Patent and Trademark Office*